(12) United States Patent
Hwang et al.

(10) Patent No.: US 10,130,312 B2
(45) Date of Patent: Nov. 20, 2018

(54) MEDICAL IMAGING APPARATUS AND METHOD OF CORRECTING MEDICAL IMAGE DATA BASED ON OUTPUT DISPLAY CHARACTERISTICS IN ORDER TO MINIMIZE DISCREPANCIES BETWEEN THE IMAGE DATA AND THE IMAGE DISPLAYED

(71) Applicant: SAMSUNG MEDISON CO., LTD., Gangwon-do (KR)

(72) Inventors: Yoon Gu Hwang, Gwangmyeong-si (KR); Gil-Ju Jin, Seoul (KR)

(73) Assignee: SAMSUNG MEDISON CO., LTD., Hongcheon-gun, Gangwon-do (KR)

(*) Notice: Subject to any disclaimer, the term of this patent is extended or adjusted under 35 U.S.C. 154(b) by 214 days.

(21) Appl. No.: 14/807,536

(22) Filed: Jul. 23, 2015

(65) Prior Publication Data
US 2016/0213335 A1 Jul. 28, 2016

(30) Foreign Application Priority Data
Jan. 23, 2015 (KR) .................. 10-2015-0011051

(51) Int. Cl.
*A61B 5/00* (2006.01)
*G06F 3/00* (2006.01)
(Continued)

(52) U.S. Cl.
CPC .......... *A61B 5/748* (2013.01); *A61B 5/0013* (2013.01); *A61B 5/7435* (2013.01); *A61B 8/464* (2013.01);
(Continued)

(58) Field of Classification Search
None
See application file for complete search history.

(56) References Cited

U.S. PATENT DOCUMENTS
2008/0097203 A1 4/2008 Nereson et al.
2008/0267467 A1 10/2008 Sokulin et al.
(Continued)

FOREIGN PATENT DOCUMENTS
KR 10-0393020 B1 7/2003
WO 2013175337 A1 11/2013

OTHER PUBLICATIONS

Extended European Search Report dated Jun. 2, 2016 issued in European Patent Application No. 15171089.4.
(Continued)

*Primary Examiner* — Kent Chang
*Assistant Examiner* — Benjamin Morales Fernandez
(74) *Attorney, Agent, or Firm* — McDermott Will & Emery LLP

(57) ABSTRACT

Disclosed herein is a medical imaging apparatus and a control method for the same, particularly a technology configured to correct and convert medical image data. Therefore, based on medical image data acquired by a medical imaging apparatus performing medical imaging diagnosis, an image having the same quality as an image outputted on a display unit of the medical imaging may be outputted on other display device.
The medical imaging apparatus includes a medical image acquisition unit acquiring medical image data of an object and a memory unit storing output image information of display device and display device information including the type of display device outputting a medical image of the object.

9 Claims, 9 Drawing Sheets

(51) Int. Cl.
*G06F 3/041* (2006.01)
*A61B 8/00* (2006.01)
*G01S 7/52* (2006.01)
*G06F 19/00* (2018.01)
*G16H 40/63* (2018.01)
*A61B 6/00* (2006.01)
*A61B 8/08* (2006.01)

(52) U.S. Cl.
CPC .......... *G01S 7/52053* (2013.01); *G06F 3/002* (2013.01); *G06F 3/0412* (2013.01); *G06F 19/00* (2013.01); *G06F 19/321* (2013.01); *G16H 40/63* (2018.01); *A61B 6/464* (2013.01); *A61B 8/5215* (2013.01)

(56) References Cited

U.S. PATENT DOCUMENTS

| | | | |
|---|---|---|---|
| 2012/0069020 A1 | 3/2012 | Smith-Casem | |
| 2012/0229526 A1 | 9/2012 | Holmes et al. | |
| 2013/0328878 A1* | 12/2013 | Stahl | G06F 3/1431 345/428 |
| 2014/0015946 A1 | 1/2014 | Yanagidate | |
| 2015/0091779 A1* | 4/2015 | Li | G06F 3/1423 345/1.3 |

OTHER PUBLICATIONS

European Office Action dated Jun. 5, 2018 issued in European Patent Application No. 15171089.4.

* cited by examiner (a)

(b)

(a)

(b)

(a) Level 1

(b) Level 2

(c) Level 3

(d) Level 4

(e) Level 5

(f) Level 6

(a)

(b)

(a)

(b)

MEDICAL IMAGING APPARATUS AND METHOD OF CORRECTING MEDICAL IMAGE DATA BASED ON OUTPUT DISPLAY CHARACTERISTICS IN ORDER TO MINIMIZE DISCREPANCIES BETWEEN THE IMAGE DATA AND THE IMAGE DISPLAYED

CROSS-REFERENCE TO RELATED APPLICATION(S)

This application claims the benefit of Korean Patent Application No. 10-2015-0011051, filed on Jan. 23, 2015 in the Korean Intellectual Property Office, the disclosure of which is incorporated herein by reference.

BACKGROUND

1. Field

Embodiments of the present disclosure relate to a medical imaging apparatus and a control method for the same, particularly, when a medical image is outputted on a display device other than a medical imaging apparatus configured to perform medical imaging diagnosis, an apparatus and a method configured to allow the medical image outputted from the display device to have the same quality as an image outputted on a display unit of the medical imaging apparatus.

2. Description of Related Art

Medical imaging apparatus are apparatuses that noninvasively acquire images of the inside of an object by emitting X-rays or applying magnetic field to the object. Medical imaging apparatuses include ultrasound imaging apparatuses, magnetic resonance imaging (MRI) apparatuses, computed tomography (CT) apparatuses, single-photon emission computed tomography (SPECT) apparatuses, positron emission tomography (PET) apparatuses, and tomosynthesis apparatuses.

Particularly, the medical imaging apparatus may generate three dimensional (3D) volume data as well as two dimensional (2D) sectional plane images of an object. A user may figure out morphological features of the inside of the object by using 3D volume data and thus the 3D volume data may be useful in diagnostic applications.

In addition, researches and developments of apparatuses and methods, which are configured to allow a user to easily procedure an object while watching a 3D image, and configured to provide more realistic medical image of an object to a patient through various display devices when simple examining or having procedure with an invasion, have been actively proceeded.

SUMMARY

Therefore, it is an aspect of the present disclosure to provide a medical imaging apparatus configured to improve convenience and reliability in medical imaging diagnosis by correcting medical image data outputted on various display devices by using the type and output image information of a display device outputting a medical image, and a control method of the same.

Additional aspects of the present disclosure will be set forth in part in the description which follows and, in part, will be obvious from the description, or may be learned by practice of the disclosure.

In accordance with one aspect of the present disclosure, a medical imaging apparatus includes a medical image acquisition unit acquiring medical image data of an object and a memory unit storing output image information of display device and display device information including the type of display device outputting a medical image of the object.

The medical imaging apparatus may further include a processor correcting medical image data outputted on a display device by using output image information, which is corresponding to the type of display device outputting the medical image of the object, among the stored output image information of display device.

The memory unit may store output image information including luminance, color temperature, gamma, illuminance, brightness, and contrast value of a medical image outputted on the display device.

The processor may automatically convert an image so that medical image data, which is corrected by using output image information corresponding to the type of the display device, is outputted on the display device.

The processor may determine the type of display device outputting the medical image of the object.

The medical imaging apparatus may further include an input unit receiving an input of display device information including the type of display device, and output image information of the display device.

The input unit may further receive an input to update the display device information and the output image information of display device.

The medical imaging apparatus may further include a communication unit transmitting the corrected medical image data to a display device.

The communication unit may receive the display device information and the output image information of display device, and receive the updated display device information and output image information of display device.

In accordance with one aspect of the present disclosure, a control method of a medical imaging apparatus performing medical imaging diagnosis by acquiring medical image data of an object includes determining the type of display device outputting a medical image of the object, and correcting medical image data outputted on a display device by using output image information corresponding to the type of the determined display device among pre-stored output image information of display device.

The control method may further include automatically converting an image so that medical image data, which is corrected by using output image information corresponding to the type of the display device, is outputted on the display device.

The control method may further include receiving an input of display device information including the type of display device, and output image information of the display device.

The receiving of an input of output image information of display device may include receiving an input of output image information including luminance, color temperature, gamma, illuminance, brightness, and contrast value of a medical image outputted on the display device.

The receiving of an input of display device information and output image information of the display device may further include receiving an input to update display device information and output image information of display device.

BRIEF DESCRIPTION OF THE DRAWINGS

These and/or other aspects of the disclosure will become apparent and more readily appreciated from the following description of embodiments, taken in conjunction with the accompanying drawings of which.

DETAILED DESCRIPTION

Figure 1:
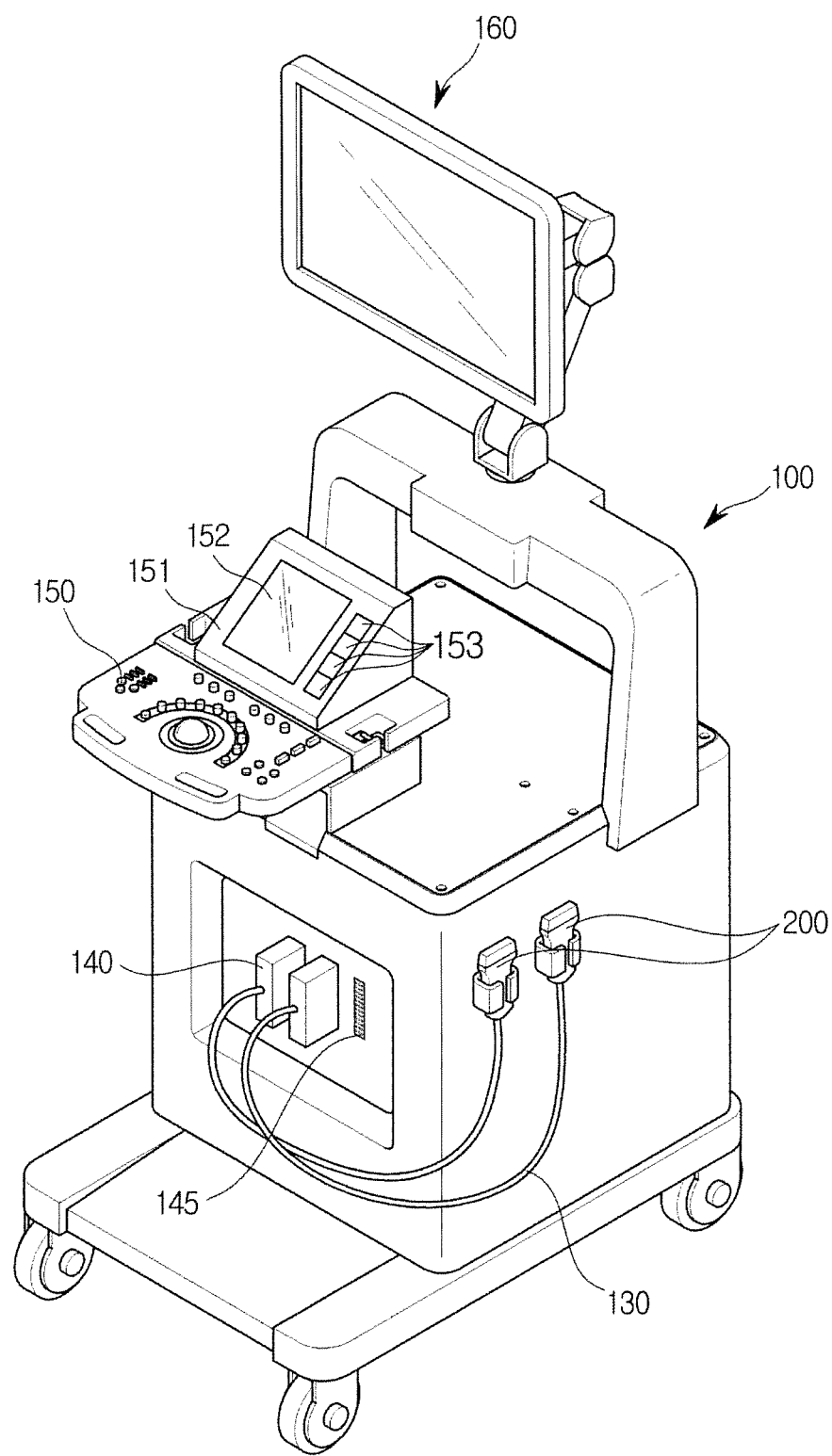
FIG. 1 is a view illustrating an exterior of an ultrasound imaging apparatus in accordance with an embodiment of the present disclosure.

The present disclosure will now be described more fully with reference to the accompanying drawings, in which exemplary embodiments of the disclosure are shown.

Embodiments disclosed in the present disclosure and configurations illustrated in drawings are merely preferable examples of the present disclosure. It should be understood that various modifications replaceable to the embodiments and the drawings of the present disclosure are available at the application time of the present application.

Hereinafter a medical imaging apparatus and a control method of the same will be described in detail according to embodiments with reference to the accompanying drawings. Same reference numerals in the drawings may represent same elements, and a duplicate description of thereof will be omitted.

Diagnostic apparatuses, in which technologies related to a medical imaging apparatus and a control method of the same according to an embodiment may be applied or may be used, may represent any one of X-ray imaging apparatus, X-ray fluoroscopic apparatus, CT scanners, magnetic resonance imaging equipment (MRI), positron emission tomography apparatus, and an ultrasonic diagnostic apparatus, an ultrasound imaging apparatus will be described as an example in the description of the embodiment, but is not limited thereto. An ultrasound imaging apparatus irradiates ultrasonic waves generated by a transducer of a probe from a surface of an object toward a target part inside the object, and noninvasively obtains images about a target part inside the object, such as a tomogram of a soft tissue or bloodstream, by receiving echo signals reflected from the object. Particularly, an ultrasonic imaging apparatus is used for medical purposes, such as observing inside an object, detecting a foreign material in object, and measuring an injury.

Such an ultrasonic imaging apparatus is compact, inexpensive, displaying a diagnostic imaging immediately and having high safety due to no risk of radiation exposure as compared with another type of diagnostic imaging apparatus, e.g., X-ray device, Computerized Tomography (CT) scanner, Magnetic Resonance Image (MRI), diagnostic nuclear medical apparatus. Therefore, the ultrasonic imaging apparatus is widely used in medical as well as imaging diagnostic apparatuses When ultrasound diagnosis is performed by using an ultrasound imaging apparatus, an ultrasound image may be outputted through various display devices, and at this time it may be important that an ultrasound image having the same quality as an ultrasound image acquired by the ultrasound imaging apparatus is outputted regardless of a type and output image characteristics of a display device.

Hereinafter the term of "user" or "examiner" may represent medical professional, such as a doctor, a nurse, a medical technologist, a medical imaging specialists, a technician to service for the medical device, but is not limited thereto.

The present disclosure is related to a medical imaging apparatus and a control method of the same, and a diagnosis by an ultrasound imaging apparatus according to one embodiment of the present disclosure will be described as an example. According to a conventional technology, when an ultrasound image of an object diagnosed by an ultrasound imaging apparatus is outputted through various display devices, an ultrasound image may be differently outputted according to the type and output characteristics of a display device. That is, although an ultrasound image outputted from a display unit of an ultrasound imaging apparatus is the same as an ultrasound image outputted from other display device, there may be differences in brightness and resolution between two ultrasound images. Therefore, when a user or an examinee identifies the ultrasound image outputted from other display device, they may see incorrect or blur image. According to one embodiment of the present disclosure, in a state of storing information related to the type and output characteristics of various display devices other than a display unit of an ultrasound imaging apparatus, when an ultrasound image is outputted from other display device, differences in an image caused by differences between the ultrasound imaging apparatus and other display device may be corrected. That is, by using output image information corresponding to the type of display device, in which an ultrasound image is outputted, ultrasound image data may be corrected. An image is automatically converted so that an ultrasound image is outputted from other display device based on the corrected data or a medical image is outputted from other display device based on the corrected data and thereby differences between an image outputted from the display unit of the ultrasound imaging apparatus and an image outputted from other display device may be minimized FIG. 1 is a view illustrating an exterior of an ultrasound imaging apparatus in accordance with an embodiment of the present disclosure.

As illustrated in FIG. 1, an ultrasound imaging apparatus 100 may include a main body, a display unit 160 connected to the main body, an input unit 150, an input device 151, and an ultrasound probe 200.

On a lower portion of the main body, a plurality of caster (not shown) may be provided for the mobility of an ultrasonic apparatus. The plurality of caster may fix the ultrasound imaging apparatus 100 to a certain location, or may move the ultrasound imaging apparatus 100 toward a certain direction. The ultrasound imaging apparatus 100 may be a cart-type ultrasound imaging apparatus.

Unlike an ultrasound imaging apparatus 100 of FIG. 1, the ultrasound imaging apparatus 100 may be a portable ultrasonic apparatus configured to be hand-held when moving at a long distance. In this case, the portable ultrasound apparatus may not be provided with the caster. The portable ultrasound apparatus may be in a type of PACS viewer, small phone, lap top computer, personal digital assistant (FDA), tablet personal computer, but is not limited thereto.

The ultrasound probe 200 may be a portion making contract with a surface of an object, and may send/receive ultrasonic waves to/from the object. Particularly, the ultrasound probe 200 may generate ultrasonic waves according to input pulses, may send the ultrasonic waves to the inside of the object and may receive echo ultrasonic waves reflected from a target part of the inside of the object.

The main body may transmit ultrasonic signals to the ultrasound probe 200 and may receive echo ultrasonic signals from the ultrasound probe 200, and may generate an ultrasound image based on the echo ultrasonic signals.

The generated ultrasound images may be provided to a user through the display unit 160. The user may diagnose an object that is a patient or an examinee by visually examining an ultrasound image of the inside of the object, which is provided from the display unit 160.

The display unit 160 may display various user interface (UI) related to the control of the ultrasound imaging apparatus. The user may check UI provided through the display unit 160 and may input control commands related to the ultrasound imaging apparatus 100 or a component of the ultrasound imaging apparatus 100 through the input unit 150.

In addition, the display unit 160 may display ultrasound images acquired during an ultrasound diagnosis. The display unit 160 may be realized by one of devices disclosed in embodiments, such as Cathode Ray Tube (CRT), and Liquid Crystal Display (LCD). The display unit 160 may provide 3D images as well as 2D images.

The input unit 150 may receive commands related to operations of the ultrasound imaging apparatus. The user may input a command to start ultrasonic examination, select a target part, select a diagnostic position, select a mode for an output ultrasound image, etc., through the input unit 150. In accordance with an embodiment, the input unit 150 may be provided on an upper portion of the main body, as illustrated in FIG. 1. The input unit 150 may include at least one of a button, a switch, a key, a wheel, a joy stick, a trackball, and a knob.

The input unit 150 may further include the input device 151 provided with a touch screen 152. The input device 151 may include the touch screen 152 and a mechanical input unit 153. A user may input data related to 3D ultrasound images outputted from the ultrasound imaging apparatus 10 through the touch screen 152 or the mechanical input unit 153. At this time, the touch screen 152 may be realized by a touch panel and a user may input a control command by touching the touch screen 152.

The touch screen 152 may display information related to the operation of the ultrasound imaging apparatus 100. For example, the touch screen 152 may display menus and guidance needed for setting the ultrasound imaging apparatus 100 and may display a current set of the ultrasound imaging apparatus 100.

The touch screen 152 may be realized by a Liquid Crystal Display (LCD), a Light Emitting Diodes (LED), an Organic Light Emitting Diodes (OLED), etc.

The ultrasound probe 200 may be connected to one end of a cable 130, and the other end of the cable 130 may be connected to a male connector 140. The male connector 140 connected to the other end of the cable 130 may be physically coupled to a female connector 145 of the main body.

According to the above-described method, the single ultrasound probe 200 may be connected to the single main body, or a plurality of ultrasound probes 200 may be connected to the single main body in a similar manner. For this purpose, a plurality of female connectors may be installed in the main body. FIG. 1 illustrates a case when two ultrasound probes 200 may be connected to the single main body.

Unlike FIG. 1, the ultrasound probe 200 may be connected to the main body through a wireless communication. In this case, the ultrasound probe 200 may perform wireless transmission of echo ultrasound signals corresponding to echo ultrasonic waves received from an object ob to the main body.

The ultrasound probe 200 may transmit or receive ultrasonic waves to or from an object ob by making contact with a surface of the object. Particularly, the ultrasound probe 200 may emit ultrasonic waves to the inside of the object according to ultrasound signals which is electrical signals provided from the main body. The ultrasound probe 200 may collect echo ultrasonic waves reflected from a certain part inside the object ob and may transmit echo ultrasound signals corresponding to the echo ultrasonic waves to the main body For this purpose, the ultrasound probe 200 may include a transducer and a MUltipleXer (MUX) circuit. The transducer may include a plurality of elements configured to convert electrical signals into ultrasonic waves or convert ultrasonic waves into electrical signals by vibrating. The plurality of elements may be arranged on a surface of the ultrasound probe housing. Particularly, a plurality of transducers may be arranged in parallel to an opening unit so that transmission or reception of ultrasonic waves may be performed through the opening unit provided on a surface of the housing.

Figure 2:
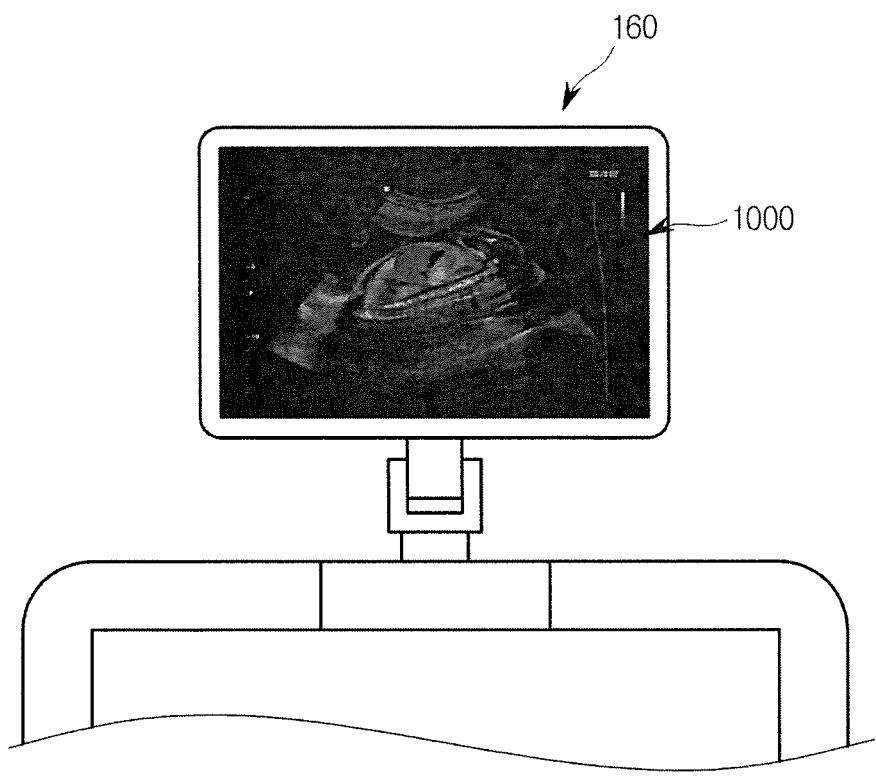
FIG. 2 is a view illustrating a display unit of an ultrasound imaging apparatus configured to output an ultrasound image of an object.

FIG. 2 is a view illustrating a display unit configured to output an ultrasound image of an object, of an ultrasound imaging apparatus.

As illustrated in FIG. 2, when an ultrasound diagnosis about an object is performed, an ultrasound image of an object may be outputted from the display unit 150 of the ultrasound imaging apparatus 100. An ultrasound image displayed on the display unit 160 of FIG. 2 is an ultrasound image 1000 of fetus, and is a screen in which ultrasound image data of fetus acquired by ultrasound diagnosis is applied. An ultrasound image outputted on the ultrasound imaging apparatus 100 may be examined by a user and an examinee, and may be corresponding to an output screen, in which the most accurate ultrasound image 1000 information of fetus is applied.

Figure 3:
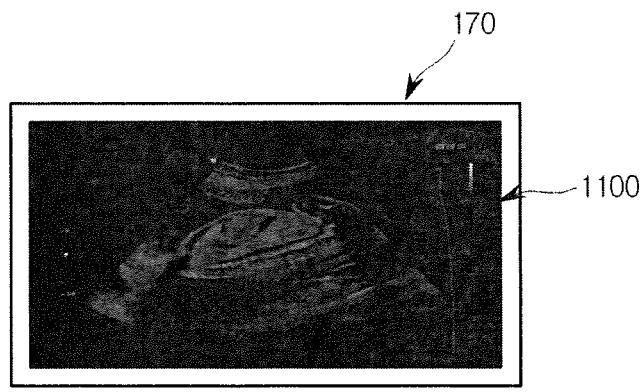
FIGS. 3 and 4 are views illustrating a screen in which an ultrasound image of an object is outputted by other display device.
Figure 3:
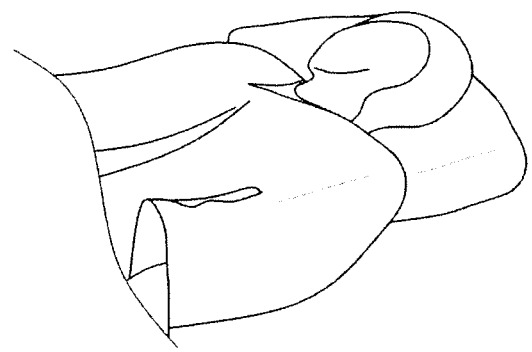
Figure 3:
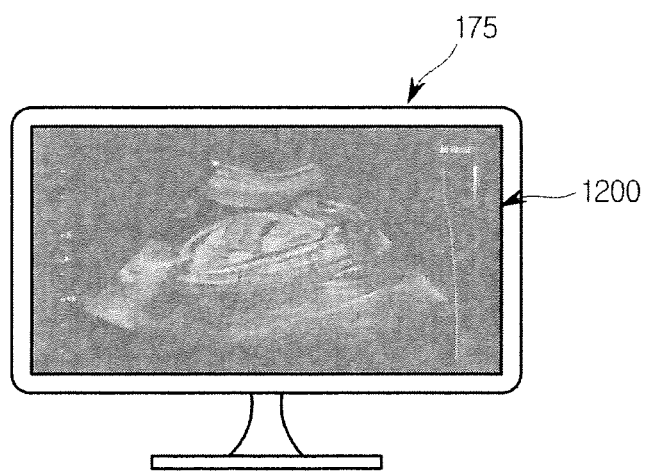
Figure 4:
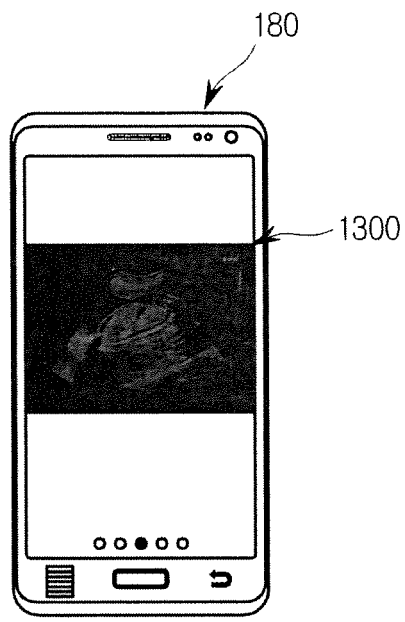
Figure 4:
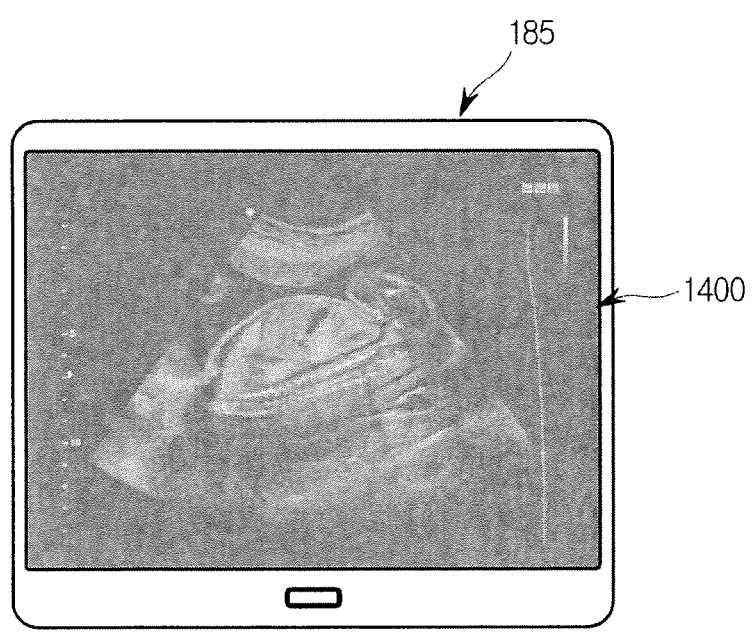

FIGS. 3 and 4 are views illustrating a screen in which an ultrasound image of an object is outputted by other display device.

In FIGS. 3 and 4, when other display device displays an ultrasound image other than an ultrasound imaging apparatus, an ultrasound image outputted on a display device 170 which is mountable to a wall or ceiling, a monitor-type display device 175 which is used to a TV or a computer, a mobile display device 180, such as a mobile phone, or a display device 185, such as a tablet, is described as an example, but there is no limit to the type of display device. Therefore, there may be various embodiments since any display device configured to output an image may be used.

Values corresponding to output image information of display device may include luminous intensity, luminance, illuminance, color temperature, gamma, brightness, contrast value, and the like, and in addition, may further include additional output image information according to the type of a display device. In addition, values of output image information, which is needed according to manufacturing process of a display device or an output image, may be added.

'Luminous intensity' of a display device means the amount of light emitted from a light source emitting light in a certain direction, and unit thereof uses candela (cd). That is, it refers to the amount of light passing through a unit area per a unit time, wherein the unit area is far from the light source of the display device by a unit distance and placed in perpendicular to a direction of light. Since the brightness of the light is determined by the size of the extent to stimulate the senses of the human eye, it may be not possible to be bright as the absolute light energy is large. Therefore, the unit of luminous intensity may be determined by selecting a certain light source, which is emitted under certain conditions, as a standard In a display device, a concept of 'luminance' is mainly used than luminous intensity. 1 cd represents a light amount of approximately a single candle (1 candle=1.067 cd), and at this time, luminance is defined as a brightness of reflector surface of a light or a light source having a certain range. That is, a concept of the luminance instead of luminous intensity is used even when a spreading of the light source is large, which may not be ignored, compared to an observation distance and thus it is not be considered as a point light source. In general, luminance is expressed by nit ($cd/m^2$) indicating a value of cd per 1 $m^2$ m and by stilb indicating $cd/m^2$. As luminance of a display device may be differently set according to usage and service environment of a display device and the type of a display panel, a LCD monitor may provide a luminance of about 200~300 nit, a LCD TV may provide an average of about 300~500 nit, a smart mobile phone may provide a luminance of about 200~700 nit depending on a used display device. Luminance of a display device may seem relatively brighter or darker depending on illuminance of the surroundings. When a user sees a screen which is too dark or too bright, the user' eyes may be easily tired, and thus display device manufacturers manufacture display devices in accordance with the usage and service environment of a display device.

Illuminance represents luminous flux, which is projected on any surface, divided by an area of the surface. That is, illuminance represents luminous flux density at a point included in the incident surface, and the unit is lux. Illuminance means brightness shined on a surface of an object, and although it is not the amount of light entering eyes, the shape looks different when the reflectance of an object is different even in the same illuminance.

Color temperature means color of light represented by temperature, and black body as a reference point may be displayed as absolute temperature 0 k. Unit of color temperature is displayed in Kelvin (K) and as the color temperature is higher, the color temperature is tinged with blue, and the color temperature is lower, the color temperature is tinged with red. For example, a candle light is 1800K, heated fluorescent lamp is 4000K, sunlight is 5500~6500K, which is close to white. When setting white light in a display device, a color temperature of 6500K, which is the standard illuminant, is used as a reference. Therefore, since the image quality of display device may vary in accordance with the color temperature, the color temperature may be an important element as output image information of the display device.

In general, Gamma is widely used as a term of gamma correction, and gamma correction represents a function of correcting a brightness level value of relatively dark scene when watching an image on a display device under bright light. That is, bright parts of an image are left as it is, and the reproduction level of dark parts is increased so that the dark parts are fully reproduced.

Contrast value is a factor of determining information on bright parts in an output image of a display device. When contrast value is large, a screen is bright and cool, color of dark parts is revived, but information of the bright parts may be white and thus nothing is visible. Conversely, when contrast value is small, information of the dark parts may be crushed while a screen is cramped and becomes darker. Thus, as for a display device, adjusting contrast value and brightness at the same time is an important fact for outputting image Other than the above, output image information related to an output image of the above-mentioned display device, according to a video adapter and a graphic processing unit, both of which are included in a display device outputting the medical image, there may differences in an output medical image. Particularly, the video adapter is an electronic component configured to generate an image signal and transmit to a monitor outputting an image through a cable, may be referred to as Graphics Card, Video Graphics Array (VGA) card, or the likes. According to the type of an adapter, a component installed in the surrounding and characteristics are different, but the video adapter basically includes video chip, video memory, Digital Analog Converter (DAC) and BIOS. The video chip is a place for calculation process, and the video memory is a place to generate an image. As the amount of memory is larger, resolution of a monitor outputting images may be increased. The DAC is a device configured to convert an analog signal into a digital signal, and the BIOS is a place in which program routine informing information of video adapter and basic input/output is stored. Graphic Processing Unit (GPU) is a component of the graphic card, and is a processor, which directly generates an image signal to be transmitted to a monitor or a display. That is, the GPU is the most important component to determine a graphic performance and resolution of a computer or other display device. That is, there may be differences in resolution of medical images outputted from various display devices depending on video adapter or GPU, and there may be differences in processing speed and outputting images of 3D medical images. Components included in display device information have no limit, and thus all of information affecting an output image may be included.

As illustrated in FIG. 3(a), an ultrasound image acquired through an ultrasound diagnosis by using the ultrasound imaging apparatus 100, may be outputted by other display devices other than the display unit 160 of the ultrasound imaging apparatus 100, and a display device of FIG. 3(a) illustrates a display device 170 mounted to a wall or a ceiling and configured to allow a patient, who is subject to an ultrasound diagnosis, to check an ultrasound image while the patient lies with taking a posture to take an examination. An ultrasound image of fetus 1100 outputted from the display device 170, may be darker than the ultrasound image 1000 outputted from the display unit 160. That is, despite of outputting the same ultrasound image diagnosed by the ultrasound imaging apparatus 100, since characteristics of outputting image of the display device 170 mounted to the wall or the ceiling are different from that of the display unit 160 of the ultrasound imaging apparatus 100, the ultrasound image 1100 may seem to be darker. Particularly, brightness of characteristics of the display device 170 illustrated in FIG. 3(a) may be displayed to be darker than that of the display unit 160 of the ultrasound imaging apparatus 100, or due to differences in set values during manufacturing process of a display device, the ultrasound image 1100 outputted from the display device 170, as illustrated in FIG. 3(*a*) may be outputted to be darker.

As illustrated in FIG. 3(*b*), an ultrasound image acquired through an ultrasound diagnosis by using the ultrasound imaging apparatus 100, may be outputted by a monitor-type display device 175 usable for a general TV or a computer monitor. An ultrasound image of fetus 1200 outputted from the display device 175 illustrated in FIG. 3(*b*), may be less clear than the ultrasound image 1000 outputted from the display unit 160 of the ultrasound imaging apparatus 100. That is, despite of outputting the same ultrasound image diagnosed by the ultrasound imaging apparatus 100, since characteristics of outputting image of the monitor-type display device 175 are different from that of the display unit 160 of the ultrasound imaging apparatus 100, the ultrasound image 1200 may seem to be less clear. In a case where the ultrasound image of fetus 1200 outputted from the display device 175 is less clear than the ultrasound image 1000 outputted from the display unit 160 of the ultrasound imaging apparatus 100, information needed for diagnosis, such as the presence of abnormalities in the fetus and the like, may not be identified on an output screen. Therefore, when outputting an ultrasound image on the monitor-type display device 175, the ultrasound image may be outputted after correcting ultrasound image data so that the ultrasound image is outputted to have the same definition as that of the display unit 160 of the ultrasound imaging apparatus 100.

As mentioned above, since there are differences in brightness or definition between the ultrasound images outputted from the display devices 170 and 175 of FIGS. 3(*a*) and (*b*), and the ultrasound image outputted from the display unit 160 of the ultrasound imaging apparatus 100, a user or a patient watching the display devices 170 and 175 may not identify precise diagnosis information about the ultrasound image. Accordingly, an ultrasound image may be needed to be outputted after correcting image data according to the type of display device.

As illustrated in FIG. 4(*a*), an ultrasound image acquired through an ultrasound diagnosis by using the ultrasound imaging apparatus 100 may be outputted by a mobile display device 180 such as a mobile phone. In recent, an ultrasound image may be outputted or identified by a mobile display device 180 such as a mobile phone, but there may be differences in outputted images depending on manufacturer and the type of a display panel. Therefore, characteristics of outputting image according to differences in the type of the mobile display device 180 and the display panel may be pre-stored and then an image having the same quality as the ultrasound image outputted from the display unit 160 of the ultrasound imaging apparatus 100 may be outputted by correcting image data according to a device to be used to output an image. An ultrasound image of fetus 1300 outputted from the display device 180 of FIG. 4(*a*) may be darker than the ultrasound image 1000 outputted from the display unit 160 of the ultrasound imaging apparatus 100 of FIG. 2. Accordingly, before transmitting the ultrasound image through the display device 180 of FIG. 4(*a*), correcting image data may be needed according to characteristics of outputting image of the display device 180 of FIG. 4(*a*).

As illustrated in FIG. 4(*b*), an ultrasound image acquired through an ultrasound diagnosis by using the ultrasound imaging apparatus 100 may be outputted by a tablet-type display device 185. An ultrasound image of fetus 1400 outputted from the display device 185 of FIG. 4(*b*) may be less clear than the ultrasound image 1000 outputted from the display unit 160 of the ultrasound imaging apparatus 100 of FIG. 2. That is, as mentioned in FIG. 3, despite of outputting the same ultrasound image of fetus diagnosed by the ultrasound imaging apparatus 100, since characteristics of outputting image of the tablet-type display device 185 are different from that of the display unit 160 of the ultrasound imaging apparatus 100, the ultrasound image 1400 may seem to be less clear.

As mentioned in FIG. 3, since there are differences in brightness or definition between the ultrasound images outputted from the display devices 180 and 185 of FIGS. 4(*a*) and (*b*), and the ultrasound image outputted from the display unit 160 of the ultrasound imaging apparatus 100, a user or a patient watching the display devices 180 and 185 may not identify precise diagnosis information about the ultrasound image. Accordingly, an ultrasound image may be needed to be outputted after correcting image data according to the type of display device.

Figure 5:
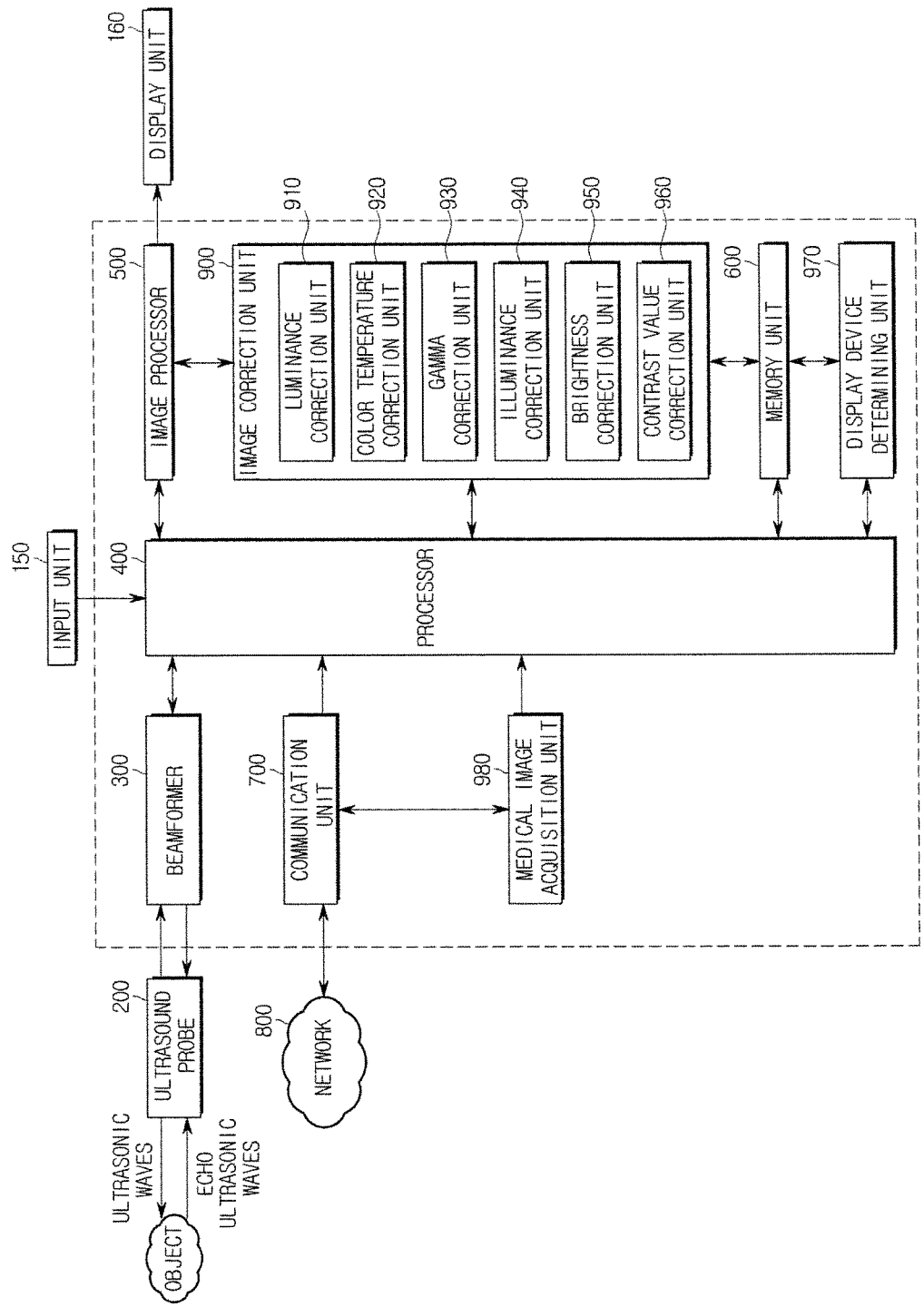
FIG. 5 is a control block diagram of an ultrasound imaging apparatus in accordance with an embodiment of the present disclosure.

FIG. 5 is a control block diagram illustrating an ultrasound imaging apparatus in accordance with an embodiment of the present disclosure.

Referring to FIG. 5, an ultrasound imaging apparatus 100 in accordance with an embodiment of the present disclosure may include an ultrasound probe 200, a beamformer 300, a processor 400, an image processor 500, a memory unit 600, a communication unit 700, an image correction unit 900, a display device determining unit 970, a medical image acquisition unit 980.

The ultrasound probe 200 may be realized in various manner configured to acquire volume data of an object. The ultrasound probe 200 may be a part to make contact with a surface of an object and may transmit or receive ultrasonic waves to or from the object. Particularly, the ultrasound probe 200 may generate ultrasonic waves according to input pulses and may transmit the ultrasonic waves to the inside of the object. The ultrasound probe 200 may receive echo ultrasonic waves reflected from a certain part inside the object.

The beamformer 300 may perform beamforming so that ultrasonic waves transmitted or received to or from the ultrasound probe 200 may be focused. The beamformer 300 may include a transmit beamformer (not shown) and a receive beamformer (not shown), and may convert analog signals into digital signals or vice versa. The beamformer 300 may adjust a time difference of ultrasound waves which are transmitted or received to or from at least one transducer. As illustrated in FIG. 1, the beamformer 300 may be included in the body of the ultrasound imaging apparatus 100, but alternatively the beamformer 300 may be provided in the ultrasound probe 200 to perform function thereof. The beamformer 300 may employ any of the known beamforming method, a beamforming method by combining a plurality of methods or selectively employ a beamforming method.

The processor 400 may receive beamforming data from the beamformer 300, and may transmit data to allow the image processor 500 to perform image processing. In addition, the processor 400 may allow data inputted from the input unit 150 to be stored in the memory unit 600, and may correct ultrasound image data outputted on a display device by using output image information corresponding to the type of display device outputting an ultrasound image of an object among output image information of various display devices stored in the memory unit 600 in accordance with an embodiment. In order to correct ultrasound image data, the processor 400 may control the image correction unit 900, and may determine that which display device outputs an ultrasound image by controlling the display device determining unit 970. The processor 400 may control to output corrected ultrasound image data through various display devices and the display unit 160 of the ultrasound imaging apparatus 100, and in addition, the processor 400 may automatically convert image data so that medical image data, which is stored in the memory unit 600 after corrected by using output image information corresponding to the type of display device, may be outputted through various display devices.

The image processor 500 may generate ultrasound images by processing beamformed echo ultrasound signals. The image processor 500 may process echo ultrasound signals according to any of the known imaging processing method. For example, the image processor 500 may perform Time Gain Compensation (TGC) on beamformed echo ultrasound signals. And then the image processor 500 may set Dynamic Range (DR). After setting Dynamic Range (DR), the image processor 500 may compress echo ultrasound signals in the set dynamic range. At last, after rectifying echo ultrasound signals, the image processor 500 may remove noisy. By using the processed echo ultrasound signals, the image processor 500 may generate ultrasound images. The image processor 500 may generate various ultrasound images. Particularly, the image processor 500 may include Amplitude Mode (A-Mode) images, Brightness Mode (B-Mode) images, Motion Mode (M-mode) images, Doppler Mode images. The image processor 500 may include one or a plurality of processor. A processor may be implemented by an array of multiple logic gates, a combination with general-purpose microprocessors and memory in which programs capable of being implemented in the microprocessors is stored. For example, the image processor 500 may be realized by general-purpose graphic processing unit (GPU).

In accordance with an embodiment, an ultrasound image signal of an object acquired by the ultrasound probe 200 may be outputted in the real time, and by the medical image acquisition unit 980, a medical image, a still ultrasound image or video data acquired by other display device may be acquired and outputted. In addition, ultrasound image data, which is acquired by the ultrasound probe 200 and stored in advance, may be used as data to output an ultrasound image. According to the type of medical imaging apparatus, the medical image acquisition unit 980 may acquire data, such as a X-ray image, MRI image, CT image, and the like, and the data may be acquired by the communication unit 700, or may be inputted through the input unit 150. Further, the medical image acquisition unit 980 may acquire Digital Imaging and Communications in Medicine (DICOM) file, and may correct an image based on display device information by storing the above-mentioned medical image data in the memory unit 600, and the medical image data may be used to convert the corrected image to be outputted on other display device.

The memory unit 600 may store a medical image acquired by the medical acquisition unit 980, ultrasound image data acquired by the ultrasound probe 200, output image information of various display devices to output an ultrasound image according to an embodiment, and information related to display devices including the type of the display device.

As mentioned above, output image information of display device may include information, such as luminous intensity, luminance, illuminance, color temperature, gamma, contrast value and the like. Since the same ultrasound image data may be outputted as an ultrasound image having different quality according to the type of display device and characteristics of outputting image, output image information allowing the most proper image corresponding to a display device to be outputted may be stored. That is, when an ultrasound image acquired by the ultrasound imaging apparatus 100 is outputted through a certain display device, set values, such as luminous intensity, luminance, illuminance, color temperature, gamma, contrast value, may be pre-stored to output the same ultrasound image as an ultrasound image outputted from the display unit 160 of the ultrasound imaging apparatus 100. Information of display device stored in the memory unit 600 may include the type of display device to output an ultrasound image, the type of display panel, manufacturer, operation principle, and the like. In addition, as mentioned in FIG. 3, device information related to a video adapter and GPU of a display device outputting a medical image may be included.

Further, the memory 600 may store ultrasound image data which is corrected according to the type of display device outputting an ultrasound image, data which is to be outputted through other display device by being converted based on the corrected ultrasound image data, output image information of display devices, or updated device information and updated output image information of display device when device information and output image information of display device are updated.

The memory unit 600 may include high-speed random access memory, magnetic disk, SRAM, DRAM, ROM, etc, but is not limited thereto. In addition, the memory unit 600 may be detachably installed on the ultrasound imaging apparatus 100. For example, the memory unit 600 may include Compact Flash Card, Secure Digital Card, Smart Media Card, Multimedia Card (MMC), or Memory Stick, but is not limited thereto. The memory unit 600 may be provided on the outside of the ultrasound imaging apparatus 100, and may transmit or receive data to or from the ultrasound imaging apparatus 100 through wired or wireless communication.

The image correction unit 900 may correct an ultrasound image to be outputted through various display devices by the control of the processor 400. That is, an ultrasound image data acquired to diagnose by the ultrasound imaging apparatus 100 may be corrected by applying output image information corresponding to a display device to output the image. For example, when an ultrasound image outputted from the mobile display device 180 such as a mobile phone, is outputted to be dark according to characteristics of outputting image of the mobile display device 180, the image may be adjusted to be image data having brighter values based on the type and output image information of the mobile display device 180. In order to adjust image data by applying various output image information of a display device, the image correction unit 900 may include a luminance correction unit 910, a color temperature correction unit 920, a gamma correction unit 930, an illuminance correction unit 940, a brightness correction unit 950, and a contrast value correction unit 960. The correction units are not limited thereto, as illustrated in FIG. 5 and there may be various embodiments. In addition, when display device information and output image information are updated, components included in the image correction unit 900 may perform correction in association with updated information. The components included in the image correction unit 900 may perform the correction about a single characteristic or about a plurality of characteristics. The image data corrected by the image correction unit 900 may be stored in the memory unit 600, and the processor 400 may control the corrected image data so that the corrected image data is outputted through a display device corresponding to the corrected image data. In addition, the processor 400 may automatically convert image data so that a medical image data, which is corrected by using output image information corresponding to a display device and stored in the memory 600, is outputted through various display devices.

The display device determining unit 970 may determine that which display device outputs an ultrasound image under the control of the processor 400. As mentioned above, since device information and output image information may be differently stored depending on which display device outputs an ultrasound image, image data may be corrected by using stored output image information corresponding to the display device when the display device determining unit 970 judges and determines a display device to output an image. Which display device outputs an image may be inputted trough the input unit 150 from a user, or may be determined based on learning data about previously outputting an image. When the display device determining unit 970 determines a display device to output an image, the processor 400 may correct image data by controlling the image correction unit 900.

The input unit 150 may receive device information and output image information of display device from a user. In addition, the input unit 150 may perform reception for updating device information and output image information of display device. That is, when device information and output image information of display device are updated, such as added, deleted, and modified, the user may input the corresponding information through the input unit 150, and the information may be applied when performing the correction.

The communication unit 700 may transmit/receive image data between the ultrasound imaging apparatus 100 and other display device. That is, the communication unit 700 may transmit ultrasound image data corrected by the image correction unit 900 to other display device via a wireless communication and may receive image information outputted from the display device. In addition, through a network 800, the communication unit 700 may receive device information and output image information of display device stored on other medical imaging apparatus or on on-line, and may receive updated device information and output image information of display device.

The display unit 160 may output an ultrasound image of an object acquired by the ultrasound imaging apparatus 100. In addition, according to an embodiment of the present disclosure, the display unit 160 may output image data, which is corrected by applying output image information of display device.

Figure 6:
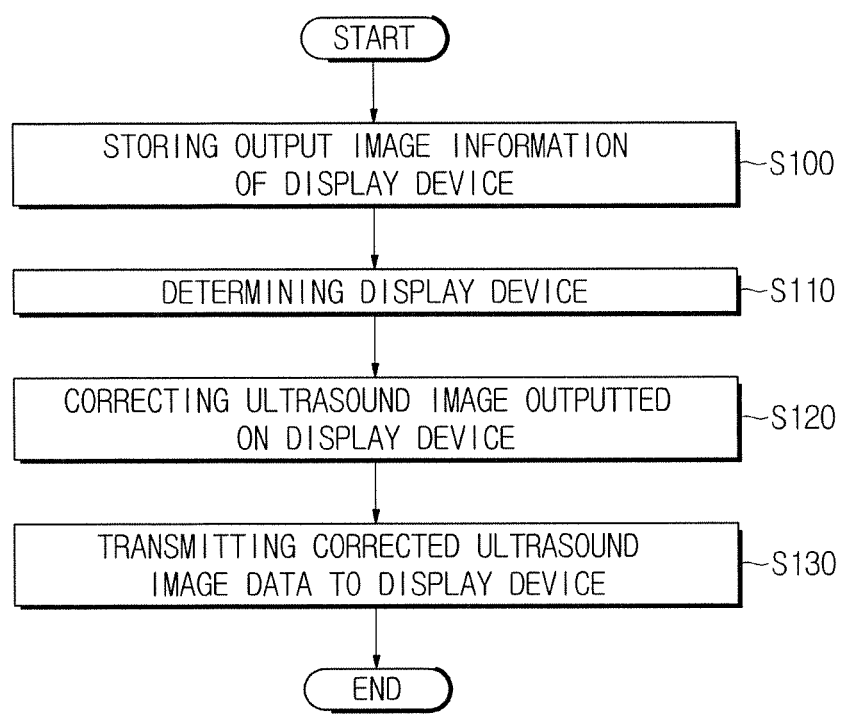
FIG. 6 is a flow chart illustrating a control method of an ultrasound imaging apparatus in accordance with an embodiment of the present disclosure.

FIG. 6 is a flow chart illustrating a control method of an ultrasound imaging apparatus in accordance with an embodiment of the present disclosure.

As mentioned in FIG. 6, a control method of an ultrasound imaging apparatus in accordance with an embodiment will be described with reference to FIGS. 7 to 9.

Before ultrasound diagnosis, output image information and device information of display device to output an ultrasound image may be stored in the memory unit 600 S 100. As mentioned above, the output image information may include luminous intensity, luminance, illuminance, color temperature, gamma, brightness, and contrast values, and may include device information related to video adapter and GPU of display device outputting a medical image, but the output image information is not limited thereto. In addition, the display device information may include the type of display device to output an ultrasound image and a display panel, and the information may be updated. A user may input output image information and display device information according to a display device through the input unit 150, and under the control of the processor 400, output image information and display device information stored on the network 800 may be received through the communication unit 700 and stored in the memory unit 600. When output image information of display device and device information of display device are updated, the updated information may be stored. Values correcting image data based on the stored information, in which the image data is to output on a display device, may be stored and then the values may be used when an image is outputted on the same display device.

The display device determining unit 970 may determine that which display device outputs an ultrasound image under the control of the processor 400 S 110. Since device information and output image information may be differently stored depending on a display device to output an image, image data may be corrected by using stored output image information corresponding to the display device when a display device to output an ultrasound image is determined by the display device determining unit 970.

The image correction unit 900 may correct ultrasound image data to be outputted on a display device by the control of the processor 400 S 120. The image correction unit 900 may include the luminance correction unit 910, the color temperature correction unit 920, the gamma correction unit 930, the illuminance correction unit 940, the brightness correction unit 950, and the contrast value correction unit 960, and may correct values, which are needed, based on display device information and output image information.

Figure 7:
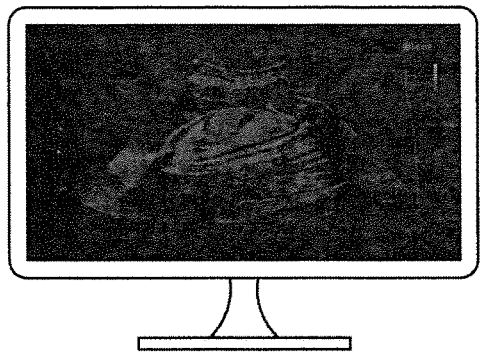
FIG. 7 is a view illustrating an ultrasound image, which is outputted by a monitor-type display device, corrected according to brightness level, in accordance with an embodiment of the present disclosure.
Figure 7:
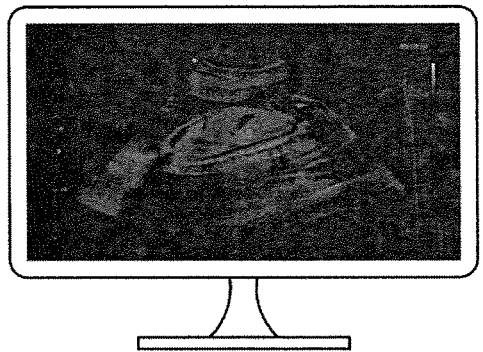
Figure 7:
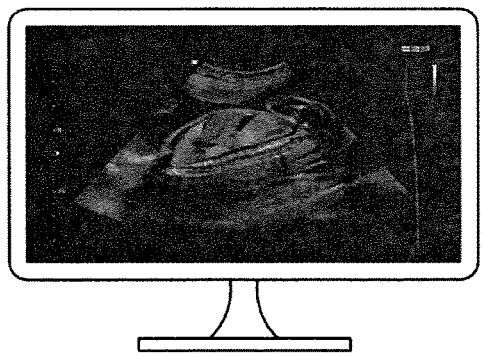
Figure 7:
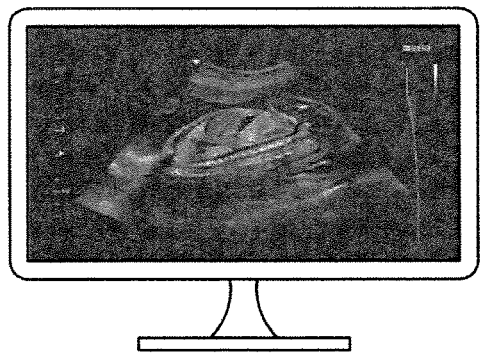
Figure 7:
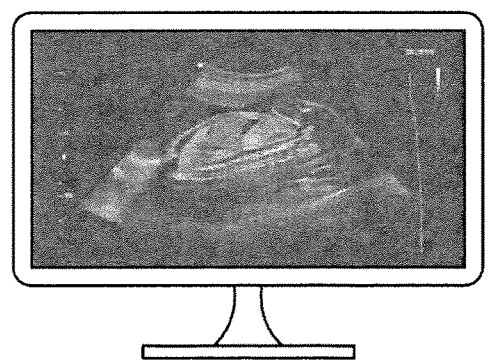
Figure 7:
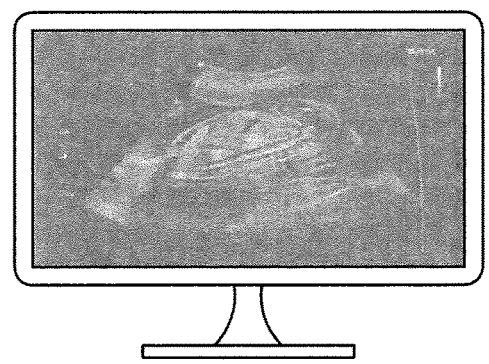

FIG. 7 is a view illustrating an ultrasound image, which is outputted by a monitor-type display device and is corrected according to brightness level in accordance with an embodiment of the present disclosure.

As mentioned in FIGS. 3 and 4, an ultrasound image may be outputted to be darker or less clear according to characteristics and output image information of display device, and thus the correction may be needed. As illustrated in FIG. 7, when an ultrasound image outputted on the display device 175 is outputted to be darker than an ultrasound image outputted on the display unit 160 of the ultrasound imaging apparatus 100, levels related to brightness characteristics may be adjusted so that the ultrasound image is outputted to be bright. In FIG. 7, a value of brightness characteristics is described as an example, but there is no limit to values of output image information applicable to an image. FIG. 7(*a*) to (*f*) illustrates a brightness of each output image when a brightness level is set to from 1 to 6. As proceeding from level 1 to level 6, an image is changed from dark to bright. When a brightness level is set to 3, as illustrated in FIG. 7(*c*), an image having the same quality as an image outputted on the display unit 160 of the ultrasound imaging apparatus 100 may be outputted. This is caused by mechanical characteristics and output image information of the monitor-type display device 175 as illustrated in FIG. 7. Under the control of the processor 400, the image correction unit 900 may correct image data based on pre-stored information of the monitor-type display device 175 so that an ultrasound image, as illustrated in FIG. 7(*c*) may be outputted. That is, the brightness correction unit 950 of the image correction unit 900 may correct a brightness value of ultrasound image data to be level 3, as illustrated in FIG. 7(*c*), and may store the brightness value on the memory unit 600, and the processor 400 may control the corrected ultrasound image data so that the corrected ultrasound image data is transmitted to the display device and an image is outputted S 130.

The corrected image data may be transmitted to the display device through the communication unit 700.

Figure 8:
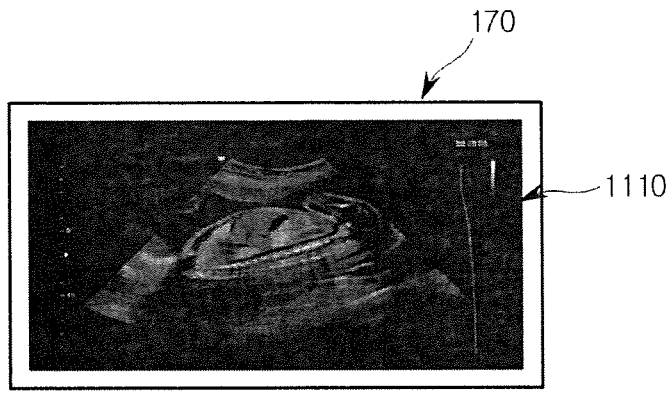
FIGS. 8 and 9 are views illustrating corrected ultrasound image data outputted by a display device.
Figure 8:
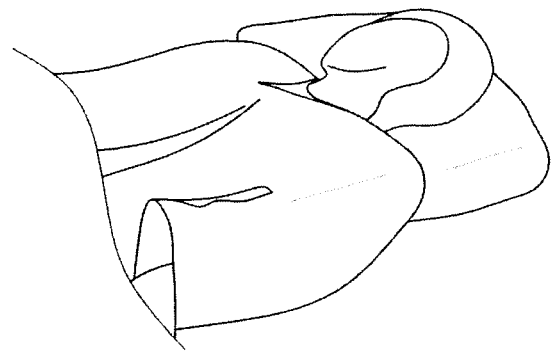
Figure 8:
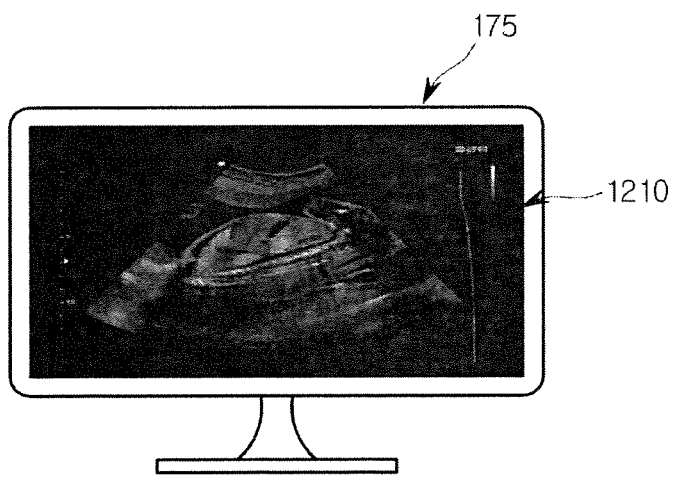
Figure 9:
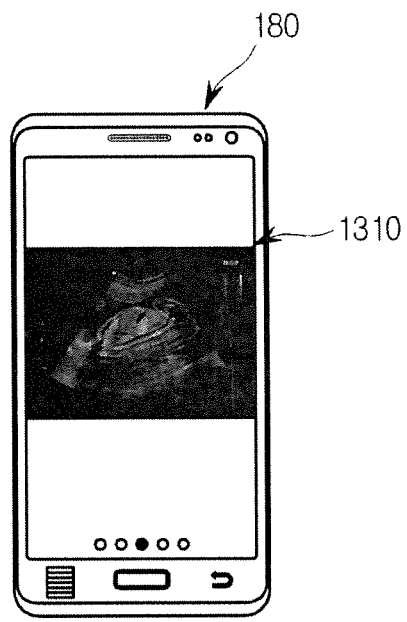
Figure 9:
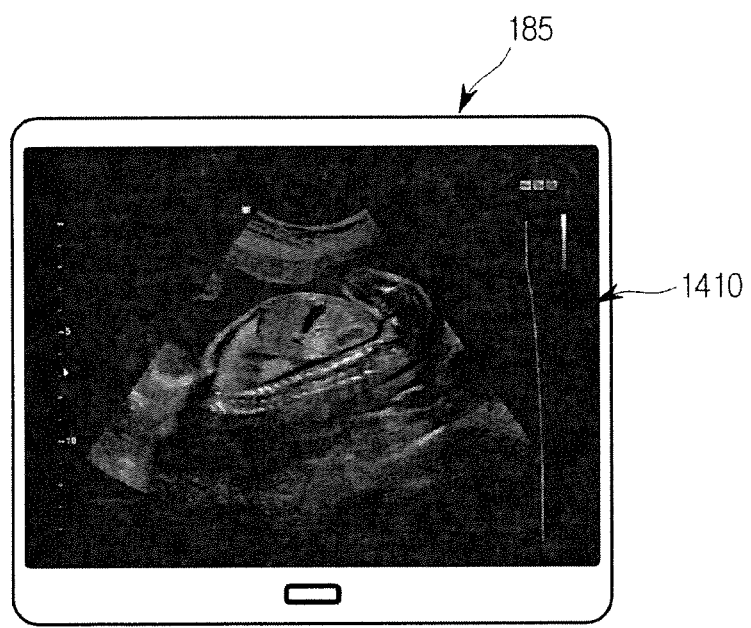

FIGS. 8 and 9 are views illustrating that corrected ultrasound image data are outputted on a display device.

FIG. 8(*a*) illustrates that an image, which has the same quality as an image outputted on the display unit 160 of the ultrasound imaging apparatus 100 of FIG. 2, is displayed on the display device 170. FIG. 8(*b*) illustrates that corrected image is displayed on the monitor-type device 175. FIGS. 8(*a*) and (*b*) illustrates that ultrasound image data, in which a brightness is corrected according to the control method of the ultrasound imaging apparatus, as illustrated in FIG. 6, is displayed. FIG. 8(*a*) illustrates that an image outputted to be dark is corrected so that the image 1110 having the same as quality as an image 1000 outputted on the display unit 160 of the ultrasound imaging apparatus 100 of FIG. 2 is outputted. FIG. 8(*b*) illustrates that an image outputted to be less clear is corrected so that the image 1210 having the same as quality as an image 1000 outputted on the display unit 160 of the ultrasound imaging apparatus 100 of FIG. 2 is outputted. That is, an image acquired by the ultrasound imaging apparatus 100 may be precisely displayed by using ultrasound image data, which is corrected based on device information and output image information of the display devices 170 and 175, and thus the accuracy and the reliability may be improved.

FIG. 9(*a*) illustrates that an image, which has the same quality as an image outputted on the display unit 160 of the ultrasound imaging apparatus 100 of FIG. 2, is displayed on the mobile display device 180. FIG. 9(*b*) illustrates that corrected image is displayed on the tablet-type device 185. FIGS. 9(*a*) and (*b*) illustrates that ultrasound image data, in which a brightness is corrected according to the control method of the ultrasound imaging apparatus, as illustrated in FIG. 6, is displayed. FIG. 9(*a*) illustrates that an image outputted to be dark is corrected so that the image 1310 having the same as quality as an image 1000 outputted on the display unit 160 of the ultrasound imaging apparatus 100 of FIG. 2 is outputted. FIG. 9(*b*) illustrates that an image outputted to be less clear is corrected so that the image 1410 having the same as quality as an image 1000 outputted on the display unit 160 of the ultrasound imaging apparatus 100 of FIG. 2 is outputted. That is, an image acquired by the ultrasound imaging apparatus 100 may be precisely displayed by using ultrasound image data, which is corrected based on device information and output image information of the display devices 180 and 185, and thus the accuracy and the reliability may be improved.

As is apparent from the above description, according to the proposed ultrasound imaging apparatus and a controlling method of the ultrasound imaging apparatus, based on stored medical image data acquired by a medical imaging apparatus performing medical imaging diagnosis, or other diagnosis apparatus, an image having the same quality as an image outputted on a display unit of the medical imaging apparatus performing medical imaging diagnosis may be outputted on other display device. Therefore, changes, which are generated according to the type of display device outputting a medical image, in an image may be minimized.

Although a few embodiments of the present disclosure have been shown and described, it would be appreciated by those skilled in the art that changes may be made in these embodiments without departing from the principles and spirit of the disclosure, the scope of which is defined in the claims and their equivalents.

DESCRIPTION OF REFERENCE NUMERALS

100: ultrasound imaging apparatus 150 input unit
160: display unit 170: display device mountable to a wall or ceiling
175: monitor-type display device 180 mobile display device
185: tablet-type display device 600: memory unit
700: communication unit 800: network
900: image correction unit 910: luminance correction unit
920: color temperature correction unit 930: gamma correction unit
940: illuminance correction unit 950: brightness correction unit
950: contrast value correction unit 970: display device determining unit
980: medical image acquisition unit

What is claimed is:

1. A medical imaging apparatus comprising:
a medical image scanner acquiring medical image data of an object;
an input unit receiving an input of display device information including a type of a display device, and output image information of the display device;
a memory storing the output image information of the display device and the display device information including the type of the display device outputting a medical image based on the medical image data; and
a processor determining the type of the display device outputting the medical image of the object based on the display device information and the output image information of the display device, and correcting the medical image outputted on the display device by using output image information, which corresponds to the type of the display device that outputs the medical image of the object, among the stored output image information of the display device.

2. The medical imaging apparatus of claim 1, wherein the memory stores the output image information including luminance, color temperature, gamma, illuminance, brightness, and contrast value of the medical image outputted on the display device.

3. The medical imaging apparatus of claim 1, wherein the processor automatically converts an image so that medical image data, which is corrected by using the output image information corresponding to the type of the display device, is outputted on the display device.

4. The medical imaging apparatus of claim 1, wherein the input unit receives an input to update the display device information and the output image information of the display device.

5. The medical imaging apparatus of claim 1, further comprising:
a transceiver transmitting the corrected medical image data to the display device.

6. The medical imaging apparatus of claim 5, wherein the transceiver receives the display device information and the output image information of the display device, and receives the updated display device information and the updated output image information of the display device.

7. A control method of a medical imaging apparatus performing medical imaging diagnosis by acquiring medical image data of an object, the method comprising:
receiving an input of display device information including a type of the display device, and output image information of the display device;
determining the type of the display device outputting a medical image based on the received display device information and the output image information of the display device;

correcting medical image outputted on the display device by using the output image information corresponding to the type of the determined display device among pre-stored output image information of the display device; and automatically converting an image so that the medical image, which is corrected by using the output image information corresponding to the type of the display device, is outputted on the display device.

8. The control method of claim 7, wherein the receiving of the input of the output image information of the display device comprises receiving an input of the output image information including luminance, color temperature, gamma, illuminance, brightness, and contrast value of the medical image outputted on the display device.

9. The control method of claim 7, wherein the receiving of the input of the display device information and the output image information of display device further comprises receiving an input to update the display device information and the output image information of the display device.

* * * * *